(12) United States Patent
Le et al.

(10) Patent No.: US 9,560,897 B2
(45) Date of Patent: Feb. 7, 2017

(54) SHOE TESTING APPARATUS

(71) Applicant: FLEXTRONICS AP, LLC, Broomfield, CO (US)

(72) Inventors: Cat Le, San Jose, CA (US); Dennis Willie, San Jose, CA (US)

(73) Assignee: Flextronics AP, LLC, San Jose, CA (US)

( * ) Notice: Subject to any disclaimer, the term of this patent is extended or adjusted under 35 U.S.C. 154(b) by 8 days.

(21) Appl. No.: 14/576,663

(22) Filed: Dec. 19, 2014

(65) Prior Publication Data

US 2016/0174663 A1 Jun. 23, 2016

(51) Int. Cl.
*G01N 3/08* (2006.01)
*G01N 3/00* (2006.01)
*G01N 11/00* (2006.01)
*A43D 1/00* (2006.01)
*G01N 3/20* (2006.01)

(52) U.S. Cl.
CPC .. *A43D 1/00* (2013.01); *G01N 3/20* (2013.01)

(58) Field of Classification Search
None
See application file for complete search history.

(56) References Cited

U.S. PATENT DOCUMENTS

| | | | | |
|---|---|---|---|---|
| 3,005,218 A * | 10/1961 | Johnston | ............ | A43D 25/10 |
| | | | | 12/142 R |
| 3,618,372 A * | 11/1971 | Beckstrom | ............ | G01N 3/42 |
| | | | | 73/159 |
| 3,975,940 A * | 8/1976 | Brungraber | ............ | G01N 19/02 |
| | | | | 73/9 |
| 6,289,743 B1 * | 9/2001 | Norton | ............ | A43D 1/00 |
| | | | | 73/847 |
| 6,988,416 B1 * | 1/2006 | Norton | ............ | G01N 3/08 |
| | | | | 73/818 |
| 8,766,811 B2 * | 7/2014 | Spampinato | ............ | G01N 3/08 |
| | | | | 340/665 |

\* cited by examiner

*Primary Examiner* — Peter Macchiarolo
*Assistant Examiner* — Jermaine Jenkins
(74) *Attorney, Agent, or Firm* — Volpe and Koenig, P.C.

(57) ABSTRACT

A test apparatus and method for testing a shoe comprises a base, with a shoe fixture for fixing a shoe against displacement, and an actuator, including a shoe contactor, mounted to the movable portion of the actuator connected to the base so that a shoe fixed to the shoe fixture can be placed in alternating stress conditions. The movable portion of the actuator is displaceable between a first position in which the shoe contactor is positioned away from the shoe fixture and a second position in which the shoe contactor is positioned proximate to the shoe fixture to contact and deflect the shoe.

15 Claims, 4 Drawing Sheets

SHOE TESTING APPARATUS

FIELD OF INVENTION

Embodiments of the present disclosure generally relate to testing devices to measure the wear resistance of shoes and replicate the deterioration seen during various wear conditions.

BACKGROUND

Some shoe test devices are known for testing various characteristics of shoe wear and durability under a variety of usage conditions. Shoe wear may include wear to the sole, cracking or separation of various layers of the sole, or separation of materials joined using joining techniques such as adhesive bonding or stitching.

Some known shoe test devices are elaborate machines with components to simulate a wearer's lower extremity. Because of their elaborate structure, these known machines are expensive to purchase and maintain and typically involve long lead times to manufacture.

Accordingly, a need exists for a less complex shoe testing apparatus.

SUMMARY

Embodiments of a shoe testing apparatus are provided herein. In some embodiments, test apparatus for a shoe comprises a base, a shoe fixture mounted to the base for fixing a shoe against axial displacement. An actuator is connected to the base, the actuator including a shoe contactor disposed on a movable portion of the actuator, so that the actuator is displaceable between a first position in which the shoe contactor is positioned away from the shoe fixture and a second position in which the shoe contactor is positioned proximate to the shoe fixture.

In some embodiments, a method of testing a shoe comprises mounting a test shoe against axial displacement in a shoe fixture; adjusting the position of an actuator; optionally program a controller coupled to the actuator; and testing the test shoe by cycling the actuator between a first position and a second position.

Other and further embodiments of the present invention are described below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

Figure 1:
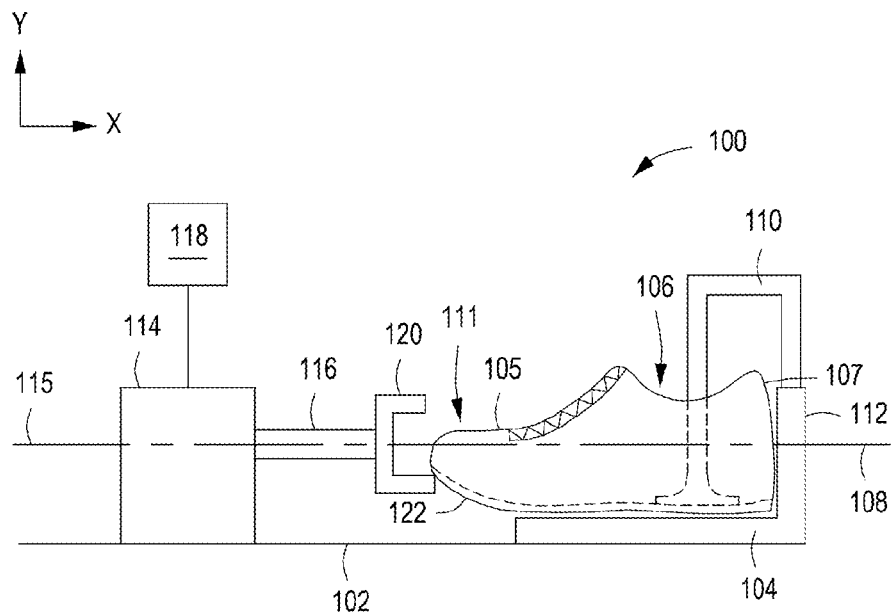
FIG. 1 is a schematic representation of a shoe testing apparatus in accordance with an embodiment of this disclosure.

To facilitate understanding, identical reference numerals have been used, where possible, to designate identical elements that are common in the figures. The figures are not drawn to scale and may be simplified for clarity. It is contemplated that elements and features of one embodiment may be beneficially incorporated in other embodiments without further recitation.

While described in reference to shoes, the present invention may be modified for a variety of applications while remaining within the spirit and scope of the claimed invention, since the range of the potential applications is great, and because it is intended that the present invention be adaptable to many such variations.

DETAILED DESCRIPTION

Certain terminology is used in the following description for convenience only and is not limiting. The words "front" and "rear" designate directions in the drawings to which reference is made. "Axially" refers to a direction along the axis of a shaft or other part. "Upper" as used in this application means the portion of a shoe above the sole that facilitates holding the shoe on a wearer's foot, unless the context clearly indicates otherwise. A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

FIG. 1 depicts a schematic representation of a shoe test apparatus 100 comprising a machine frame or base 102. The base 102 provides dimensional stability and support for the components of the testing apparatus 100. The base 102 may be formed from materials known those of ordinary skill in the art and may include metallic structural components, such as aluminum or steel extrusions, angled pieces, or machined parts. The function of the base 102 may also be provided by an industrial workshop table, or an industrial floor having adequate mechanical characteristics to support and stabilize the components.

The test apparatus 100 includes a shoe fixture 104 mounted to the base 102 for fixing a shoe 106 against displacement. The shoe 106 may be fixed against axial displacement in an axial direction aligned with a longitudinal axis 108 of the shoe 106. The fixing against axial displacement may be accomplished through a clamping device 110 with an optional back stop 112 configured to engage a heel portion 107 of the shoe 106. The clamping device 110 may be a vertical device as illustrated in the non-limiting embodiment of FIG. 1 using known mechanisms to apply a sufficient load to the shoe 106 to maintain a desired position.

Figure 2:
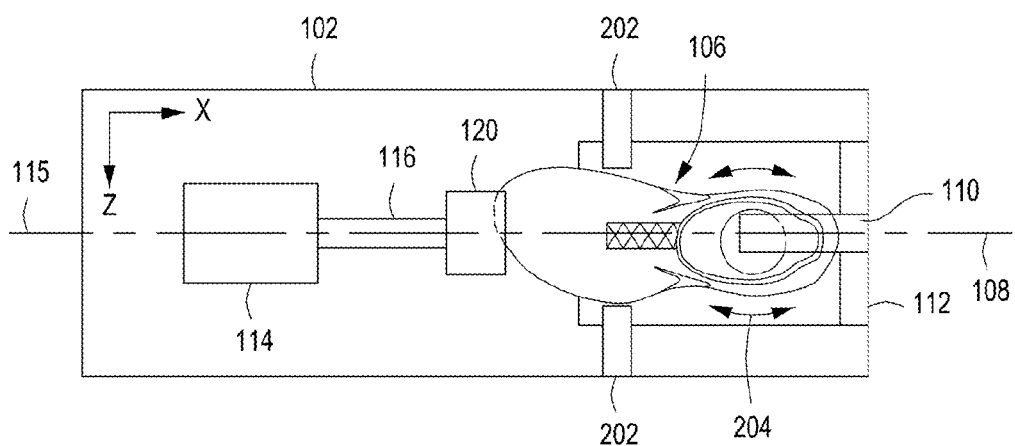
FIG. 2 depicts a top view of the apparatus of FIG. 1.

As shown in FIG. 2, additional fixing elements 202 may be included to limit lateral displacement perpendicular to the axis 108. Fixing elements 202 may also limit rotational displacement depicted by curved arrow 204 of the shoe 106 about the vertical clamp 110. Fixing elements 202 may be lateral elements with a longitudinal axis generally perpendicular to the longitudinal axis 108 of the test shoe 106 as illustrated in FIG. 2. In other embodiments, other structures can function as fixing elements. For example, in FIG. 3, rods 302 are generally perpendicular to the base 102 and can limit the lateral or rotational displacement of the shoe 106.

Returning to FIG. 1, an actuator 114 is provided, connected to the base 102. The actuator 114 may be, in non-limiting examples, a hydraulic or pneumatic cylinder, or a linear motor with a movable portion, such as actuator rod 116. The actuator 114 is adjustably connected to the base 102 so the position of the actuator 114 with respect to the shoe fixture 104 is adjustable. The actuator may be adjusted in the XY plane of FIG. 1 or in the XZ plane of FIG. 2. The actuator 114 is fixable to the base 102 in a desired position and can be repositioned as necessary.

Disposed at the end of the rod is a shoe contactor 120 which in the non-limiting embodiment of FIG. 1 has a C-shaped configuration. Other shapes for shoe contactors will be obvious to those skilled in the art.

The actuator rod 116 is displaceable between a first position in which the shoe contactor 120 is positioned away from the shoe fixture 104 as shown in FIG. 1 and a second position in which the actuator rod 116 is positioned proximate to the shoe fixture 104. In a preferred embodiment, the actuator 114 is positioned so that, in the first position, the shoe contactor 120 is spaced far enough away from the shoe fixture 104 to facilitate installation or removal of a shoe 106 from the shoe fixture, and in the second position, the shoe contactor 120 contacts and deflects the shoe 106 a desired amount. The first and second positions may be adjustably fixed, for example with a mechanical stop (not shown).

An appropriately selected actuator 114 can develop sufficient force to deflect a test shoe 106 to the desired degree. For example, some test shoes required a 100 pound force to deflect the toe portion 111 of the shoe to the desired degree. Other shoes may require a greater force, for example 180 pounds, while others may require a lesser force, for example, 75 pounds to achieve the same desired degree of deflection. By adjusting the input (e.g., air pressure, oil pressure, or current) to the actuator 114, an appropriately selected actuator can provide the required force to achieve the desired degree of deflection in the shoe 106.

In an embodiment, a test shoe 106 is mounted in the shoe fixture 104 against deflection along the longitudinal axis of the show 108. The actuator rod 116 is extended until the shoe contactor contacts the toe portion 111 of the test shoe 106 and continues extending until the toe portion 111 is at least partially compressed. In some embodiments, when the toe portion 111 is at least partially compressed, a sole portion 122 deflects towards the shoe upper 105, that is, until the toe portion 111 of the test shoe 106 deflects upwards, as drawn in FIG. 1.

Figure 3:
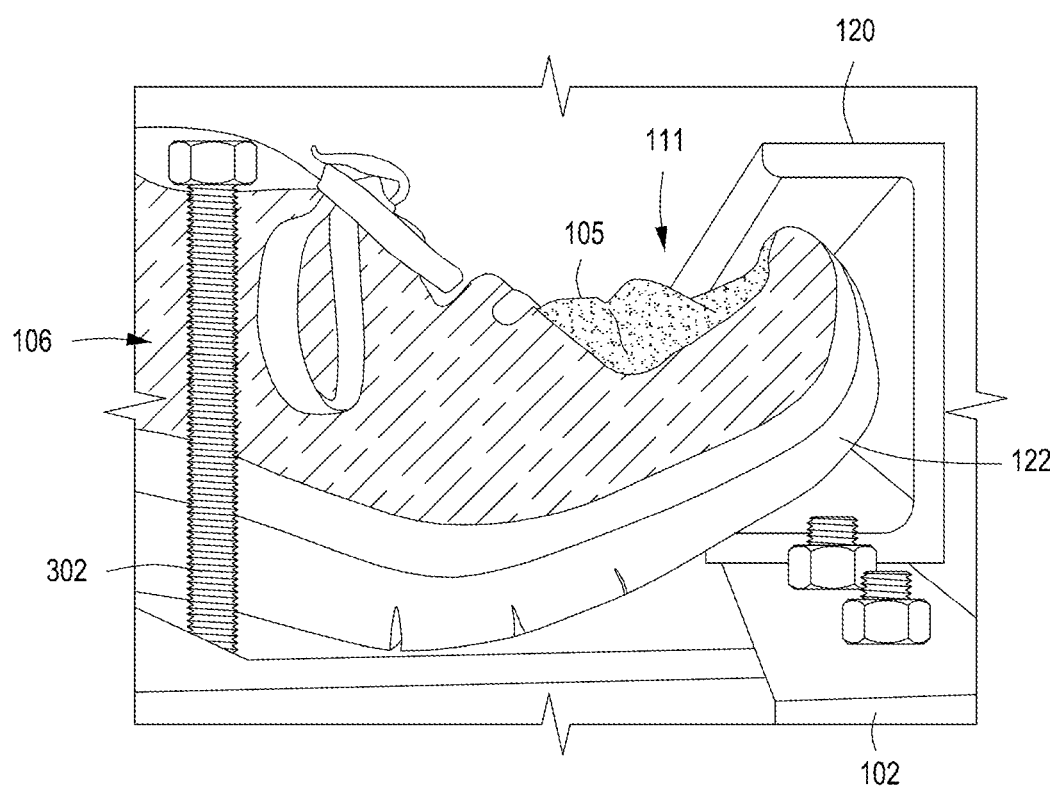
FIG. 3 is a side view of a portion of the apparatus of FIG. 1 with a shoe in a partially compressed condition.

FIG. 3 is a side view of a shoe 106 mounted to the testing apparatus of FIG. 1 showing the toe portion 111 in a partially compressed condition. The toe portion 111 is partially compressed by the shoe contactor 120 so that the sole 122 of the toe portion 111 has deflected in an upward (as draw) direction. The shoe upper 105 has become compressed and buckled while the sole 122 has elongated.

In a preferred embodiment, the actuator 114 is a double-acting air cylinder with a linearly displaceable rod 116. It may be desirable to position the actuator 114 so that the axis 115 of the rod 116 is parallel to an axis of the test shoe 106. In some embodiments, it may be desirable to position the actuator 114 so the road axis 115 is collinear with an axis 108 of the test shoe as illustrated in FIG. 1.

The actuator 114 may be electronically controlled by a programmable controller 118 to cycle between the first position and the second position. In an embodiment, the controller 118 can cycle the actuator through 60 cycles per hour, in which one cycle includes extending the rod 116 so the contactor 120 can deflect the toe portion 111 of the shoe 106, hold the shoe in a deflected position for a desired dwell period, and release the shoe 106 to return to an un-deflected state. In some embodiments of the test apparatus, an insert may be included in the shoe 106 to provide resistance to deflection and to facilitate the shoe 106 returning to the un-deflected state. If necessary for test requirements, the insert can be modeled after a human foot from a suitable material to mimic actual use conditions.

Figure 5:
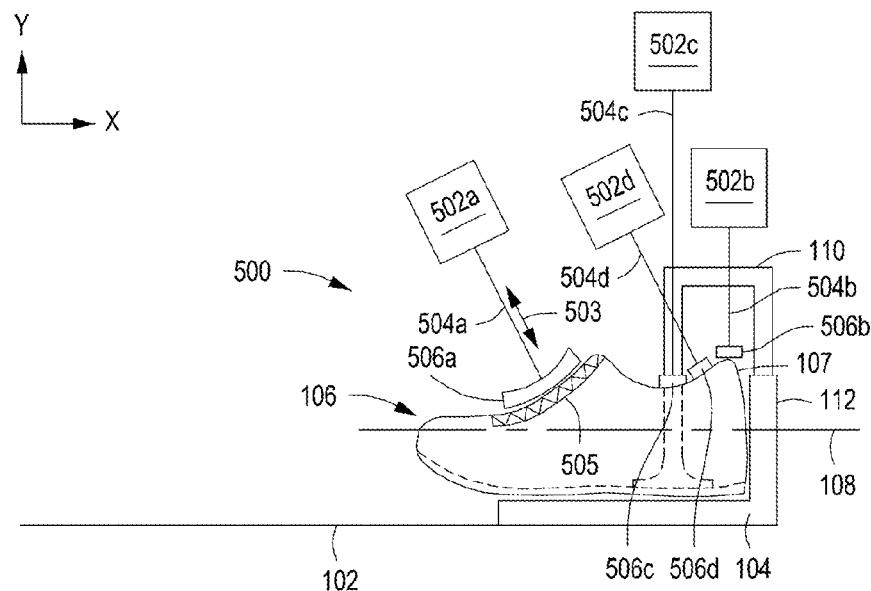
FIG. 5 is a schematic representation of a shoe testing apparatus in accordance with an embodiment of this disclosure.
Figure 6:
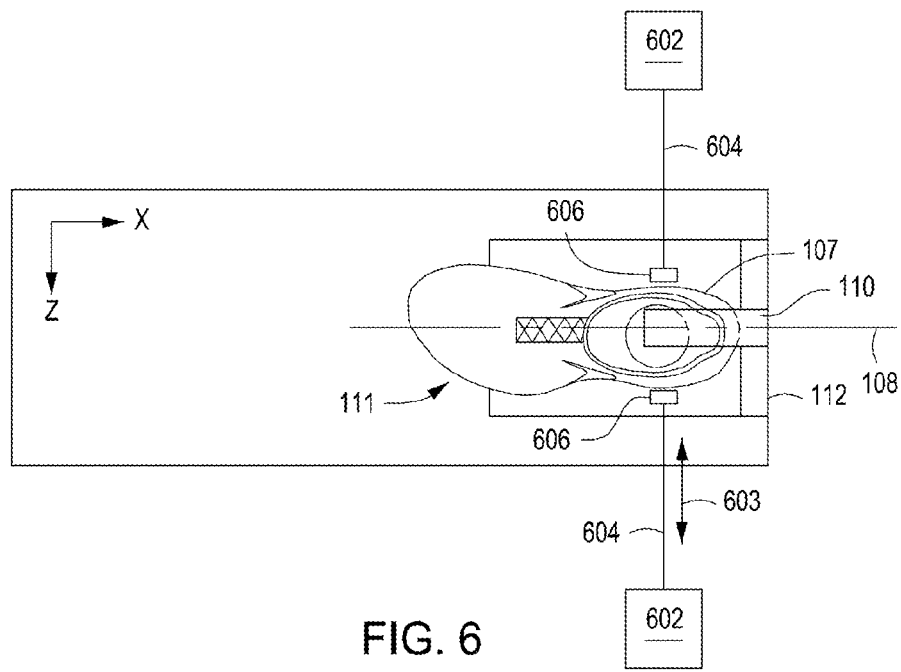
FIG. 6 is a schematic representation of a shoe testing apparatus in accordance with an embodiment of this disclosure.

FIGS. 5 and 6 schematically illustrate a shoe test apparatus 500 with components similar to the shoe test apparatus 100 of FIG. 1 with non-limiting examples of actuator arrangements which may be used in addition to, or in place of, the actuator/rod/contactor 114/116/120 arrangement of FIG. 1. As illustrated the shoe test apparatus 500 shares components such as the base 102, the shoe fixture 104, the backstop 112, and the clamp 110 with shoe test fixture 100. Other components may also be shared.

For example, contactor 506a may be connected to actuator 502a through rod 504a to contact and depress the instep area 505 of the shoe 106 as the rod 504a extends and retracts as represented by arrow 503 under the influence of the actuator 502a. The actuator 502a may be positioned at any angle to the shoe 106 and mounted to any suitable structure for stability and support. The contactor 506a may be curved as illustrated or may have other configurations. In an embodiment, the contactor 506a may include an engagement feature that can grip a portion of the shoe 106 and pull the portion as the rod 504a travels towards the actuator 502a. For example, the engagement feature may grip the shoe laces or the holes formed in the shoe to accept the laces to test a feature of the shoe 106.

In an embodiment, the contactor 506a may be configured to extend into the area of the shoe normally occupied by the wearer's foot (the "shoe interior") and pull the instep towards the actuator 502a. For example, the contactor may be U-shaped with one leg in the shoe interior and the other leg extending along a portion of the instep 505. The rod 504a may be coupled to the leg in the instep area 505 and may push, pull, or both push and pull the instep area 505 under the control of the actuator 502a.

In other non-limiting embodiments, actuators 502b-502d are similarly coupled with contactors 506b-506d via rods 504b-504d, respectively, and may be directed to shoe areas located at the heal portion 107. The contactors 506b-506d are moved via the rods 504b-504d to contact an area of the shoe 106 to compress or deflect the area as discussed above. Actuators 502b-502d may be positioned at any angle with respect to the shoe 106 and mounted to any suitable structure for stability and support.

In the non-limiting embodiment of FIG. 6, contactors 606 may be connected to actuator 602 through rod 604 to contact and depress the shoe 106 at the heal portion 107 as the rod 604 extends and retracts as represented by arrow 603 under the influence of the actuator 602. The actuator 602 is illustrated as oriented substantially perpendicular to the axis 108 of the shoe for ease of illustration only, but may be positioned at any angle to the shoe 106. The rods 604 are illustrated as generally aligned, but may be offset in the X- or Y-direction as necessary. The contactors 606 may be configured to provide compression to the heal portion 107. The contactors 606 may be configured to provide rotation of the heal portion 107 about the Y-axis.

Actuators assemblies similar to 602/604/606 may be placed at the toe portion 111 to similarly contact a portion of the shoe 106 to displace, deflect, compress, or rotate a portion of the shoe 106. In an embodiment, the contactor 606 may be configured to grip a portion of the instep 505, for example the laces or lace holes, to provide displacement in the Z-direction.

Other configuration for actuator assemblies could be similarly used at different areas of the shoe 106 for testing of other shoe characteristics.

Any combination of actuator assemblies in the non-limiting embodiments of FIGS. 1, 2, 5, and 6 may be used together to test various features of a test shoe 106. The actuators 114, 502a-502d, and 602 may drive the associated rod and contactor to contact and displace, deflect, compress, or rotate a portion of the shoe 106 in any sequence under the control of a controller, for example 118. That is, the various actuators may extend and retract the associated rods at the same time (i.e., concurrently), in sequence one after the other, or in any other pattern desired. In some embodiments, one actuator assembly may contact and deflect a portion of the shoe 106, and while still in contact with the shoe 106 to displace, deflect, compress, or rotate a portion of the shoe, a second or subsequent actuator assembly may engage and displace, deflect, compress, or rotate the same or a different portion of the shoe. Thus, the actuator assemblies can simulate a variety of usage conditions to test or investigate various characteristics of shoe wear and durability under those conditions.

The inventors have found that cycling a test shoe 106 under the conditions described and shown above can provide an accurate correlation of useful shoe life under real conditions. The test provides appropriate levels of stress to critical parts of the shoe to determine possible points of premature failure of materials (e.g., sole, last, upper) or manufacturing defects (e.g., bonding, stitching).

Figure 4:
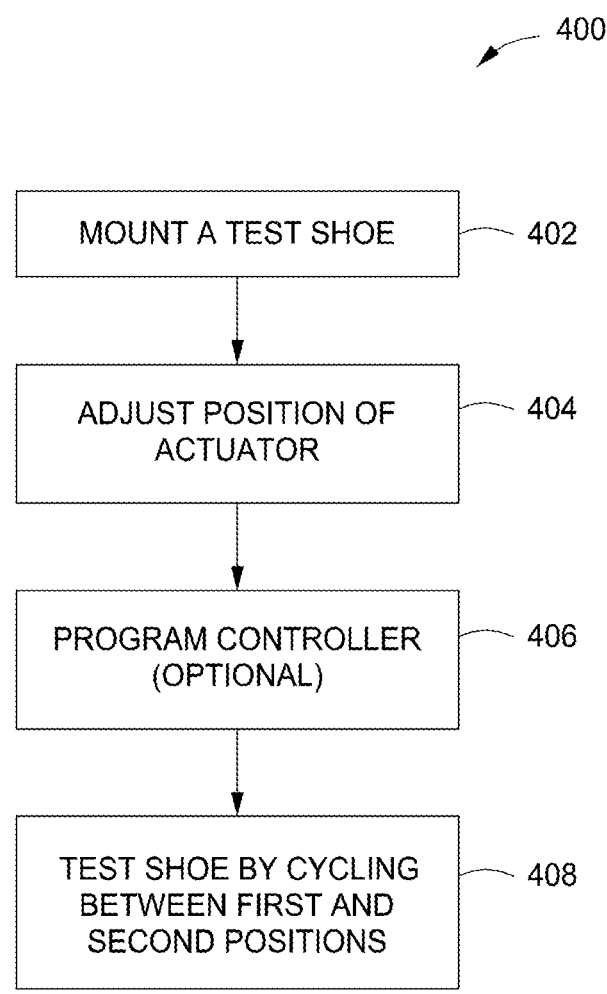
FIG. 4 is a flow diagram of a method in accordance with an embodiment of this disclosure.

FIG. 4 represents a flow diagram illustrating a method of using the above described test apparatus. At 402, a test shoe 106 is mounted to the shoe fixture 104 as described above, using one or more of the described clamp 110 or fixing elements 202. At 404, the position of the actuator 114 is adjusted to provide the desired test orientation. The actuator 114 may be adjusted to provide the correct deflection of a portion of the shoe 106 (for example a deflection of the toe portion 111) or the correct alignment of the rod axis 115 with respect to a shoe axis, e.g., 108.

At 406, a controller 118 may be programmed to provide the correct function of the actuator 114. The controller may provide the actuator 114 with the correct input and the correct timing so that the desired deflection of the shoe is achieved at the desired cycle time. At 408, testing is performed on the test shoe 106 by cycling the rod between the first and second positions.

Thus an apparatus and method of shoe testing are provided herein. The inventive shoe testing apparatus advantageously reduces the complexity of typical shoe test machines.

Having thus described the present invention in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A test apparatus for a shoe comprising:
a base;
a shoe fixture mounted to the base for fixing the shoe in place within the test apparatus and preventing the shoe from axial displacement within the test apparatus,
a first actuator connected to the base, the first actuator including a shoe contactor disposed on a movable portion of the first actuator,
wherein the movable portion of the first actuator moves parallel to a longitudinal axis of the shoe fixture and is displaceable between a first position in which the shoe contactor is positioned away from the shoe fixture and a second position in which the shoe contactor is positioned proximate to the shoe fixture.

2. The apparatus of claim 1, wherein the actuator is adjustably connected to the base so that a distance between the shoe contactor in the second position and the shoe fixture is adjustable.

3. The apparatus of claim 1, wherein the actuator is a linear actuator including an actuator rod, wherein
the actuator is connected to the base so that an axis of the actuator rod is parallel to the longitudinal axis of the shoe fixture; and
the actuator rod is linearly displaceable along the longitudinal axis of the shoe fixture.

4. The apparatus of claim 3, wherein one or more of the displacement of the actuator rod and the force exerted by the actuator rod is adjustable.

5. The apparatus of claim 1, wherein the shoe contactor in the second position contacts a part of the shoe mounted to the shoe fixture so that a portion of the shoe deflects.

6. The apparatus of claim 1, wherein the shoe contactor has a C-shaped portion to engage a toe portion of the shoe mounted on the shoe fixture to deflect a sole portion of the shoe towards a portion of the shoe upper.

7. The apparatus of claim 6, wherein the deflection is adjustable by adjusting one or more of the forces exerted by the actuator rod on the toe portion of the shoe or adjusting the extended position of the actuator rod with respect to the fixtured position of the toe portion of the shoe before contact by the shoe contactor.

8. The apparatus of claim 1, wherein the actuator is electronically controlled to cycle between the first position and the second position.

9. The apparatus of claim 1, further comprising:
a second actuator including a shoe contactor disposed on a movable portion of the second actuator,
wherein the movable portion of the second actuator is displaceable between a first position in which the shoe contactor is positioned away from the shoe fixture and a second position in which the shoe contactor is positioned proximate to the shoe fixture.

10. The apparatus of claim 9, further comprising a controller to electronically control the first actuator and the second actuator to each cycle between a first position and a second position in a predetermined manner.

11. A method of testing a shoe in a test apparatus for shoe comprising:
mounting the shoe in a shoe fixture of the test apparatus to prevent the shoe from axial displacement within the test apparatus;
adjusting the position of a first actuator;

optionally program a controller coupled to the first actuator; and testing the shoe by cycling the first actuator between a first position and a second position, wherein the first activator is linearly displaceable.

12. The method of claim 11, wherein the adjusting comprises positioning the first actuator so that an axis of a first actuator rod is parallel with a longitudinal axis of the shoe being tested.

13. The method of claim 11, wherein the adjusting comprises positioning the first actuator so that an axis of the first actuator rod is collinear with a longitudinal axis of the shoe being tested.

14. The method of claim 11, wherein, in the first position of the first actuator, the shoe is in a non-stressed condition and in the second position of the first actuator, a portion of the shoe is in a partially compressed condition.

15. The method of claim 11, further comprising:

providing a second actuator;

adjusting the position of the second actuator;

optionally program a controller coupled to the second actuator; and testing the shoe by cycling the second actuator between a first position and a second position, wherein in the first position of the second actuator, the shoe is in a non-stressed condition and in the second position of the second actuator, a portion of the shoe is in a partially compressed condition.

* * * * *